(12) United States Patent
Tsukamoto et al.

(10) Patent No.: US 9,790,140 B2
(45) Date of Patent: Oct. 17, 2017

(54) METHOD FOR PRODUCING BUTADIENE

(71) Applicant: TORAY INDUSTRIES, INC., Tokyo (JP)

(72) Inventors: Daijiro Tsukamoto, Kamakura (JP); Satoshi Sakami, Kamakura (JP); Kenji Kawamura, Kamakura (JP); Katsushige Yamada, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 15/021,540

(22) PCT Filed: Sep. 9, 2014

(86) PCT No.: PCT/JP2014/073800
§ 371 (c)(1),
(2) Date: Mar. 11, 2016

(87) PCT Pub. No.: WO2015/037580
PCT Pub. Date: Mar. 19, 2015

(65) Prior Publication Data
US 2016/0229765 A1 Aug. 11, 2016

(30) Foreign Application Priority Data
Sep. 12, 2013 (JP) ................. 2013-189018

(51) Int. Cl.
*C07C 1/24* (2006.01)
*B01J 27/18* (2006.01)
(Continued)

(52) U.S. Cl.
CPC ............. *C07C 1/24* (2013.01); *B01J 27/1806* (2013.01); *B01J 35/023* (2013.01);
(Continued)

(58) Field of Classification Search
CPC .. C07C 1/24; C07C 2527/173; C07C 2521/08
See application file for complete search history.

(56) References Cited

U.S. PATENT DOCUMENTS

| 2,444,538 | A | | 7/1948 | Seymour |
| 3,758,612 | A | * | 9/1973 | Maurin ................ B01J 27/1806 585/611 |

(Continued)

FOREIGN PATENT DOCUMENTS

| JP | 4979989 | 8/1974 |
| JP | 60126235 | 7/1985 |

(Continued)

OTHER PUBLICATIONS

International Search Report for International Application No. PCT/JP2014/073800 dated Dec. 16, 2014.

(Continued)

*Primary Examiner* — In Suk Bullock
*Assistant Examiner* — Youngsul Jeong
(74) *Attorney, Agent, or Firm* — RatnerPrestia

(57) ABSTRACT

A method for producing butadiene from 2,3-butanediol with high selectivity without using a radioactive substance is disclosed. The method for producing butadiene comprises the step of dehydrating 2,3-butanediol in the presence of a catalyst containing an alkali metal salt of phosphoric acid such as an alkali metal dihydrogen phosphate supported on silica. Preferred examples of the alkali metal herein include K, Rb, and Cs. The catalyst is preferably a catalyst prepared by calcination of the silica to which the alkali metal of phosphoric acid is attached.

5 Claims, 1 Drawing Sheet

(51) Int. Cl.
  *B01J 37/02* (2006.01)
  *B01J 37/08* (2006.01)
  *B01J 35/02* (2006.01)
  *B01J 35/10* (2006.01)
  *B01J 37/00* (2006.01)

(52) U.S. Cl.
  CPC ........ *B01J 35/1019* (2013.01); *B01J 37/0018* (2013.01); *B01J 37/0236* (2013.01); *B01J 37/08* (2013.01); *C07C 2521/08* (2013.01); *C07C 2527/167* (2013.01); *C07C 2527/173* (2013.01)

(56) References Cited

U.S. PATENT DOCUMENTS

| | | | |
|---|---|---|---|
| 3,781,222 | A | 12/1973 | Weisang |
| 3,957,900 | A * | 5/1976 | Weisang ............ B01J 27/18 568/903 |
| 9,255,041 | B2 | 2/2016 | Yano |
| 2011/0143406 | A1 | 6/2011 | Moriyama |
| 2011/0152582 | A1 | 6/2011 | Strohm |
| 2014/0238841 | A1 | 8/2014 | Kawamura |
| 2015/0361007 | A1 | 12/2015 | Millet |

FOREIGN PATENT DOCUMENTS

| | | | |
|---|---|---|---|
| JP | 2013515010 | 5/2013 | |
| JP | 2013139428 | 7/2013 | |
| JP | 2014172883 | 9/2014 | |
| KR | 1020120099818 | * 9/2012 | ............. B01J 23/04 |
| KR | 1020120107353 | 10/2012 | |
| KR | 1020140112261 | 9/2014 | |
| WO | 2007094178 | 8/2007 | |
| WO | 2009151342 | 12/2009 | |
| WO | 2012157495 | 11/2012 | |
| WO | 2013054874 | 4/2013 | |
| WO | 2014118484 | 8/2014 | |

OTHER PUBLICATIONS

Li, ZJ., et al., "Microbial production of meso-2,3-butanediol by metabolically engineered *Escherichia coli* under low oxygen condition," Aug. 2010, pp. 2001-2009, vol. 87(6), Applied Microbiology and Biotechnology (abstract only).

Multer, A., et al. "Production of methyl ethyl ketone from biomass using a hybrid biochemical/catalytic approach," 2013, pp. 56-60, vol. 52(1), Industrial & Engineering Chemistry Research (abstract only).

Written Opinion of the International Searching Authority for International Application No. PCT/JP2014/073800 dated Dec. 16, 2014.

* cited by examiner

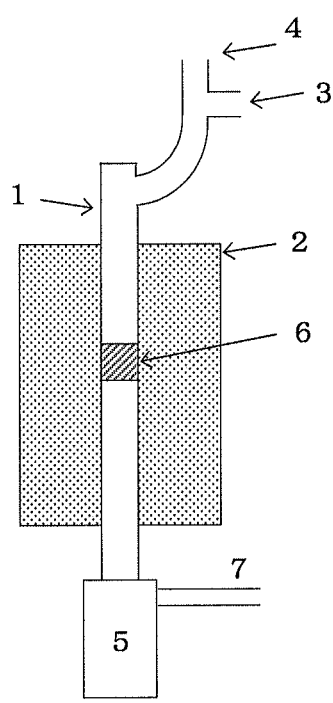

US 9,790,140 B2

METHOD FOR PRODUCING BUTADIENE

CROSS REFERENCE TO RELATED APPLICATIONS

This is the U.S. National Phase application of PCT International Application No. PCT/JP2014/073800, filed Sep. 9, 2014, and claims priority to Japanese Patent Application No 2013-189018, filed Sep. 12, 2013, the disclosures of each of these applications being incorporated herein by reference in their entireties for all purposes.

FIELD OF THE INVENTION

The present invention relates to a method for producing butadiene from 2,3-butanediol.

BACKGROUND OF THE INVENTION

Butadiene is a raw material for butadiene rubbers, styrene-butadiene rubbers, acrylonitrile-butadiene rubbers, ABS resins, and the like, and is one of the most important organic compounds in the chemical industry. Butadiene can be converted to adiponitrile, which is an intermediate for synthesis of nylon 66, chloroprene, which is a raw material for chloroprene rubber, or 1,4-butanediol, which is a raw material for polybutylene terephthalate. These polymer compounds produced using butadiene as a raw material are widely used for not only industrial goods such as automobile tires, electric wire coatings, and engineering plastics, but also daily necessaries such as clothing. Butadiene has been increasingly demanded year by year.

Butadiene is mainly produced by extraction separation from the C4 fraction generated during production of ethylene by a naphtha cracker. However, it is expected that, as the raw material of ethylene shifts to natural gas, shortage of supply of butadiene may occur in the future. In view of this, methods for producing butadiene using natural gas as a raw material have been studied in recent years. However, because of problems such as depletion of fossil resources in the future, global warming due to greenhouse gas emission, and the like, realization of sustainable butadiene production is increasingly demanded. Therefore, development of a method for producing butadiene from biomass resource-derived substances, which are renewable sources, is demanded.

2,3-Butanediol is a polyol used as a raw material for inks, perfumes, liquid crystals, insecticides, softening reagents, explosives, plasticizers, and the like. Industrially, 2,3-butanediol is produced by a method in which 2-butene oxide is hydrolyzed in an aqueous perchloric acid solution. On the other hand, since 2,3-butanediol can also be produced by microbial fermentation using as a raw material a monosaccharide such as glucose or xylose (Patent Document 1), it is a substance derivable from biomass resources. Thus, if production of butadiene by dehydration of 2,3-butanediol can be achieved, butadiene, and existing synthetic resins using butadiene as a raw material, can be replaced with biomass resource-derived substances.

It is known that dehydration of 2,3-butanediol can be carried out using an acid catalyst. For example, a method in which 2,3-butanediol is dehydrated by bringing the 2,3-butanediol into contact with Japanese acid clay has been disclosed (Non-patent Document 1). A method in which 2,3-butanediol is dehydrated by treatment in an aqueous sulfuric acid solution has also been disclosed (Non-patent Document 2). Further, a method in which 2,3-butanediol is dehydrated by bringing the 2,3-butanediol into contact with zeolite has been disclosed (Non-patent Document 3). However, the main product in these methods is methyl ethyl ketone rather than butadiene.

Methods in which butadiene is selectively produced by dehydration of 2,3-butanediol have been reported. Non-patent Document 4 discloses a method using a thorium oxide ($ThO_2$) catalyst; Patent Document 2 discloses a method using a cesium oxide-carrying silica catalyst; and Patent Document 3 discloses a method using a hydroxyapatite-alumina composite catalyst.

Butadiene can also be produced by dehydration of 1,3-butanediol. Patent Document 4 discloses a method using a catalyst composed of a mixture of sodium dihydrogen phosphate ($NaH_2PO_4$), calcium monohydrogen phosphate ($CaHPO_4$), phosphoric acid ($H_3PO_4$), and butyl amine-phosphoric acid ($BuNH_2 \cdot H_3PO_4$), wherein the selectivity of butadiene is reported to be 77%.

PRIOR ART DOCUMENTS

Patent Documents

[Patent Document 1] WO 2013/054874
[Patent Document 2] KR 10-2012-0099818 A
[Patent Document 3] KR 10-2012-0107353 A
[Patent Document 4] U.S. Pat. No. 2,444,538 B

Non-Patent Documents

[Non-patent Document 1] Journal of the Agricultural Chemical Society of Japan vol. 18, p. 143-150 (1942)
[Non-patent Document 2] Industrial Engineering Chemistry Product Research and Development, vol. 21, 473-477 (1982)
[Non-patent Document 3] Industrial & Engineering Chemistry Research, vol. 52, p. 56-60 (2013)
[Non-patent Document 4] Journal of Council Science Industrial Research in Australia, vol. 18, p. 412-423 (1945)

SUMMARY OF THE INVENTION

As described above, when 2,3-butanediol is dehydrated using an acid catalyst, methyl ethyl ketone is produced as the main product, while butadiene is hardly produced. The methods disclosed in Non-patent Document 1, Non-patent Document 2, and Non-patent Document 3 produce methyl ethyl ketone at selectivities of 66 mol %, 96 mol %, and not less than 90 mol %, respectively.

Further, as described above, methods for selectively produce butadiene from 2,3-butanediol have been reported. In the method using a thorium oxide catalyst disclosed in Non-patent Document 4, the selectivity of butadiene is 62.1 mol %. However, since thorium oxide is a radioactive substance, its industrial use is difficult.

It has been reported that, in the method disclosed in Patent Document 2, the selectivity of butadiene is 62 mol %, and the selectivity of methyl ethyl ketone is 33%. However, as shown in Comparative Example 7 of the present application, a reproducibility study for this method by the present inventors resulted in a selectivity of butadiene of as low as 32.9 mol %. Thus, the selectivity was very low.

In the method disclosed in Patent Document 3, the selectivity of butadiene is as low as 48 mol %. The selectivity of methyl ethyl ketone is 43% in this case.

Thus, in the cases where the radioactive substance, thorium oxide, is not used, no method succeeds in production of butadiene from 2,3-butanediol with high selectivity. Therefore, development of an industrially applicable method for producing butadiene has been strongly demanded.

As described above, butadiene can also be selectively produced by dehydration of 1,3-butanediol (Patent Document 4). However, Non-patent Document 1 reports that, although 1,3-butanediol easily undergoes two-molecule dehydration to become butadiene, dehydration of 2,3-butanediol using Japanese acid clay results in a selectivity of butadiene of as low as 4% and a selectivity of methyl ethyl ketone of 66%. That is, although 1,3-butanediol and 2,3-butanediol have similar chemical structures, they show very different reactivities in dehydration. It has been clearly shown that, since dehydration of 2,3-butanediol under such conditions dominantly proceeds through a pathway generating methyl ethyl ketone, selective production of butadiene is not easy.

Thus, it is clear that, although the method for selectively producing butadiene by dehydration of 1,3-butanediol has been reported, direct application of this method to dehydration of 2,3-butanediol does not necessarily allow selective production of butadiene.

An object of the present invention is to provide a method for producing butadiene from 2,3-butanediol with high selectivity without using a radioactive substance.

As a result of intensive study to solve the above problem, the present inventors discovered a method for producing butadiene by dehydrating 2,3-butanediol in the presence of a catalyst containing an alkali metal salt of phosphoric acid supported on silica, thereby completing the present invention.

That is, the present invention provides a method for producing butadiene, which method comprises the step of dehydrating 2,3-butanediol in the presence of a catalyst containing an alkali metal salt of phosphoric acid supported on silica.

In an embodiment of the present invention, the alkali metal salt of phosphoric acid is an alkali metal dihydrogen phosphate.

In an embodiment of the present invention, in cases where the alkali metal salt of phosphoric acid is an alkali metal dihydrogen phosphate, the weight ratio of the alkali metal dihydrogen phosphate to the total weight of the silica and the alkali metal dihydrogen phosphate in the catalyst is not less than 5 wt % and not more than 40 wt % before preparation of supporting the alkali metal dihydrogen phosphate on the silica.

In an embodiment of the present invention, the alkali metal in the alkali metal salt of phosphoric acid in the catalyst is one or more selected from the group consisting of K, Rb, and Cs.

In an embodiment of the present invention, the catalyst is one prepared by calcination of silica to which the alkali metal of phosphoric acid is attached, in the step of supporting the alkali metal salt of phosphoric acid on the silica.

In an embodiment of the present invention, the reaction temperature of the step of dehydrating 2,3-butanediol is not less than 380° C. and not more than 520° C.

In an embodiment of the present invention, the total content of titanium and aluminum per unit surface area of the silica support is not more than 750 ng/m².

The dehydration step for producing butadiene from 2,3-butanediol in the present invention can be described by the reaction equation below.

By the present invention, butadiene can be produced from 2,3-butanediol with high selectivity without using a radioactive substance.

BRIEF DESCRIPTION OF THE DRAWINGS

FIG. 1 is a diagram illustrating an example of a fixed-bed gas-phase flow reactor.

DETAILED DESCRIPTION OF CERTAIN EMBODIMENTS OF THE INVENTION

Representative embodiments for carrying out the present invention are described below, but the present invention is not limited to these embodiments.

In the present invention, "biomass resources" mean renewable organic resources derived from organisms, which are composed of organic matter produced by carbon dioxide fixation by plants using solar energy. Specific examples thereof include maize, sugarcane, tubers, wheat, rice, soybean, pulp, kenaf, rice straw, wheat straw, bagasse, corn stover, switchgrass, weeds, waste paper, woods, charcoal, natural rubber, raw cotton, soybean oil, palm oil, safflower oil, and castor oil.

In the present invention, the biomass resource-derived substance means a substance that is induced, that can be induced, or that was induced, from a biomass resource by fermentation, chemical conversion, or the like. In the present invention, 2,3-butanediol derived from a biomass resource or 2,3-butanediol derived from a fossil resource such as petroleum may be used as a raw material.

2,3-Butanediol can be divided into three optical isomers, that is, (2R,3R)-2,3-butanediol, (2S,3S)-2,3-butanediol, and meso-2,3-butanediol. The 2,3-butanediol in the present invention may be any of these isomers, or may be a mixture of a plurality of the isomers.

As disclosed in Patent Document 1, 2,3-butanediol derived from a biomass resource can be produced by microbial fermentation of sugars obtained from the biomass resource. Examples of microorganisms capable of fermentation using sugars as carbon sources include *Klebsiella pneumoniae, Klebsiella oxymora,* and *Paenibacillus polymyxa,* which are naturally occurring microorganisms. These microorganisms can produce (2R,3R)-2,3-butanediol and meso-2,3-butanediol. As shown in WO 2007/094178, the genus *Ochrobactrum* is capable of selective production of (2S,3S)-2,3-butanediol. Further, as described in WO 2009/151342, *Clostridium autoethanogenum* is known to be a microorganism capable of fermentation using carbon monoxide as a carbon source. 2,3-Butanediol produced from such a microorganism is also included in the 2,3-butanediol in the present invention.

Alternatively, a method using a microorganism given a capacity to produce 2,3-butanediol by genetic recombination may be employed. Specific examples of such a method include the method described in "Applied Microbiolgy and Biotechnology, vol. 87, No. 6, pp. 2001-2009 (2010)".

Examples of the carbon source in the fermentation feedstock include sugars such as glucose, fructose, sucrose, xylose, arabinose, galactose, mannose, and starch. These sugars may be commercially available products; degraded products of recycled resources, or herbaceous or woody biomasses; or degraded products of cellulose, hemicellulose or lignin materials, prepared by chemical or biological treatment. Further, in cases of the above-described *Clostridium autoethanogenum,* carbon monoxide is used as a carbon source. Carbon monoxide can be obtained by incomplete combustion of coal, petroleum or a biomass resource. Alternatively, a mixed gas with hydrogen, methane, and the like generated during formation of ironmaking coke may be used.

2,3-Butanediol derived from fossil resources is commercially available, and can be easily obtained.

The catalyst used in the present invention is described below.

In the present invention, "alkali metal salt of phosphoric acid" means the following (A), (B), or (C):

(A) an "alkali metal phosphate" represented by General Formula (I) "$M_nH_{3-n}PO_4$" (which means a monomer that has not undergone dehydration condensation);

(B) a mixture of (A) "alkali metal phosphates" having different alkali metals; or (C) a "dehydrated condensate of alkali metal phosphate" produced by dehydration condensation of all or part of phosphate groups in (A) or (B).

In General Formula (I), M represents an alkali metal, that is, Li (lithium), Na (sodium), K (potassium), Rb (rubidium), or Cs (cesium). n represents a positive real number of not more than 3. That is, the salt of "phosphoric acid" includes dihydrogen phosphate ($H_2PO_4^-$), monohydrogen phosphate ($HPO_4^{2-}$), and phosphate ($PO_4^{3-}$).

The catalyst used in the present invention can be prepared by supporting an alkali metal salt of phosphoric acid on a support. The alkali metal salt of phosphoric acid may be supported by, for example, the conventional impregnation method described in "Catalyst Handbook (Kodansha Ltd., published on Dec. 10, 2008), pp. 284-285". The impregnation method can be divided into the evaporation-to-dryness method and the equilibrium adsorption method. The evaporation-to-dryness method is a method in which a support is impregnated in an impregnation liquid containing a component to be supported, and the impregnation liquid is then removed by distillation, followed by drying and/or calcining the catalyst, thereby immobilizing the component to be supported on the support. The equilibrium adsorption method is a method in which a support is impregnated with an impregnation liquid containing a component to be supported, and the impregnation liquid is then removed by filtration, followed by drying and/or calcining the catalyst, thereby immobilizing the component to be supported on the support. Here, in the present invention, the component to be supported is an alkali metal salt of phosphoric acid, and the catalyst to be used in the present invention can be prepared by impregnating the support with an aqueous solution containing the alkali metal salt of phosphoric acid, removing water, and then drying and/or calcining the resultant.

The impregnation liquid can be simply prepared by dissolving the alkali metal salt of phosphoric acid in water. It is also possible to use, instead of the alkali metal salt of phosphoric acid, a phosphoric acid source such as ammonium dihydrogen phosphate (($NH_4$)$H_2PO_4$) or diammonium hydrogen phosphate (($NH_4$)$_2HPO_4$), and an alkali metal source such as alkali metal nitrate ($MNO_3$), alkali metal carbonate ($MCO_3$), or alkali metal hydrogen carbonate ($MHCO_2$). Unnecessary salts other than the alkali metal salt of phosphoric acid produced in such cases may be released from the catalyst as nitrogen oxide gas or carbon oxide gas during the calcination of the catalyst.

The temperature during the impregnation of the support is not limited as long as it is not more than 100° C. The impregnation is preferably simply carried out at ordinary temperature since no device or operation for cooling or heating is necessary in such a case. The impregnation liquid can be removed by distillation or filtration.

The silica to which the alkali metal phosphate is attached by impregnation with a solution of the alkali metal salt of phosphoric acid as described above can be dried by, for example, flowing air at a temperature of about 80 to 100° C. Drying of the silica under such a temperature condition enables preparation of a catalyst containing mainly the "alkali metal phosphate" of (A) or (B) described above, which has not undergone dehydration condensation, or a mixture thereof supported on silica.

In the preparation of the catalyst to be used in the present invention by supporting an alkali metal salt of phosphoric acid on silica, silica to which the alkali metal phosphate is attached by impregnation with a solution of the alkali metal salt of phosphoric acid as described above, or silica prepared by attaching the alkali metal salt of phosphoric acid thereto and drying the resultant as described above, is preferably subjected to calcination. The calcination may be carried out at a calcination temperature of not less than 300° C. and not more than 600° C., preferably at a temperature of not less than 450° C. and not more than 550° C. The atmosphere for the calcination is not limited as long as oxygen is contained therein. The calcination can be simply carried out under air flow. The calcination causes dehydration condensation of all or part of phosphate groups in the alkali metal salt of phosphoric acid, to generate a "dehydrated condensate of alkali metal phosphate" ((C) described above). The catalyst used in the method of the present invention is preferably a catalyst produced as described above by performing calcination in the step of supporting an alkali metal salt of phosphoric acid on the silica, wherein the dehydrated condensate of the alkali metal phosphate is supported on the silica.

The catalyst in the present invention may be used after molding into an arbitrary shape, if necessary. The molding may be carried out by, for example, the extrusion molding method, compression molding method, tumbling granulation method, or spray drying granulation method described in "Catalyst Handbook (Kodansha Ltd., published on Dec. 10, 2008), pp. 290-301". If necessary, a molding additive(s) may be used. In cases where an organic molding additive is used, the organic component can be removed by performing calcination under air flow after the molding of the catalyst. The calcination temperature in such a case is preferably 450° C. to 600° C.

In the present invention, the alkali metal salt of phosphoric acid supported on the support is preferably an alkali metal dihydrogen phosphate. More specifically, one of, or a mixture of two or more of, alkali metal dihydrogen phosphates selected from the group consisting of $NaH_2PO_4$, $KH_2PO_4$, $RbH_2PO_4$, and $CsH_2PO_4$ may be preferably used.

The type of the support which supports the alkali metal salt of phosphoric acid is not limited as long as the support is silica ($SiO_2$). The support allows production of butadiene with high selectivity.

Specific examples of the silica include CARiACT [Q, G, P] (Fuji Silysia Chemical Ltd.); N601, N602 (JGC Catalysts and Chemicals Ltd.); silica gel [40, 60, 100] (Merck); silica gel [60, 60N] (Kanto Chemical Co., Inc.); SUNSPHERE [H, L], M. S. GEL [DF, DM, D], SUNLOVELY [C, TZ, LFS] (AGC Si-Tech Co., Ltd.); Wakogel [C, DX, FC, G, LP, Q, S], Wakosil [C, 25SIL, 25C18, 40SIL, 40C18] (Wako Pure Chemical Industries, Ltd.); JRC-SIO-1, JRC-SIO-3, JRC-SIO-4, JRC-SIO-5, JRC-SIO-6, JRC-SIO-7, JRC-SIO-8, JRC-SIO-9 (reference catalysts of Catalysis Society of Japan); REOLOSIL [QS, MT, DM, KS, HM, PM] (Tokuyama Corporation); Mizukasil [P, SK] (Mizusawa Industrial Chemicals, Ltd.); fumed silica, silica gel [Grade 3, 12, 22, 40, 62, 922, 923], Silica, mesostructured [MSU-F, MCM-41, HMS] (Sigma-Aldrich); Davisil [Grade 633, 634, 635, 636, 643, 644, 645, 646] (W. R. Grace & Co.); Nipgel [AZ, AY, BY, CX, CY], Nipsil [NS, NA, KP, E, K, HD, L, G] (Tosoh Silica Corporation); CARPLEX [#80, BS-303, BS-306, BS-304N, BS-308N] (DSL Japan); Aerosil [90, 130, 150, 200, 255, 300, 380, OX50, TT600], Aerolyst [3041, 3045] (Evonik Industries AG); Cab-O-Sil [M-5, TS, HP, CT] (Cabot Corporation); Hi-Sil [132,135, 190, 210, 233, 243, 532, 900, 915] (PPG Industries); and Zeosil [115GR, 1115MP, 1165MP, 1205MP] (Rhodia-Solvay).

In general, silica may contain metals such as titanium and aluminum. Usually, in the present invention, silicas such as those described above which are generally available may be used as they are. For example, silica in which the total content of titanium and aluminum is not more than 1100 $ng/m^2$ per unit surface area may be used as a support for production of butadiene with high selectivity.

The catalyst used in the method of the present invention preferably has a performance which allows maintenance of high butadiene selectivity for a long time during the gas-phase flow reaction described later. In such a case, silica in which the content of metals such as titanium and aluminum is small, more specifically, silica in which the total content of titanium and aluminum is not more than 750 $ng/m^2$ per unit surface area of the silica support is preferably used as the support.

In cases where magnesia (MgO), titania ($TiO_2$), alumina ($Al_2O_3$), zirconia ($ZrO_2$), or the like is used as the support instead of the silica of the present invention, the butadiene selectivity is insufficient.

In the present invention, it is important to use the alkali metal salt of phosphoric acid in a state where it is supported on silica. In cases where an alkali metal salt of phosphoric acid which is not supported on silica is used as the catalyst, the conversion of 2,3-butanediol is decreased, and production of a large amount of 3-buten-2-ol occurs, leading to low selectivity of butadiene (see Comparative Example 5). Further, in cases where silica on which an alkali metal salt of phosphoric acid is not supported is used as the catalyst, sufficient selectivity of butadiene cannot be obtained (see Comparative Example 6).

In a catalyst in which an alkali metal dihydrogen phosphate is supported on silica, the weight ratio of the alkali metal dihydrogen phosphate to the total weight of the silica and the alkali metal dihydrogen phosphate is preferably not less than 5 wt % and not more than 40 wt %, more preferably not less than 10 wt % and not more than 40 wt %. The weight ratio of the alkali metal dihydrogen phosphate herein means the weight ratio before supporting the alkali metal dihydrogen phosphate on the silica. More specifically, the weight ratio of the alkali metal dihydrogen phosphate herein means the weight ratio of the alkali metal dihydrogen phosphate to the total weight of the silica and the alkali metal dihydrogen phosphate upon the impregnation of the silica with the impregnation liquid containing the alkali metal dihydrogen phosphate.

The alkali metal contained in the catalyst used in the present invention is more preferably one or more selected from the group consisting of K, Rb, and Cs. In cases where a catalyst containing such an alkali metal(s) is used, dehydration of 2,3-butanediol tends to result in low selectivity of methyl ethyl ketone and high selectivity of butadiene. More preferably, the catalyst prepared by supporting one or more selected from the group consisting of $KH_2PO_4$, $RbH_2PO_4$, and $CsH_2PO_4$ on the silica is used.

The amount of the catalyst containing an alkali metal salt of phosphoric acid supported on silica is not limited, and may be set appropriately. The amount is usually not less than 0.1 g, preferably not less than 0.3 g per feed rate of 2,3-butanediol of 1 g/hour. There is no upper limit of amount of the catalyst, but, from the viewpoint of the cost, the amount is usually not more than 10 g per feed rate of 2,3-butanediol of 1 g/hour.

The step of dehydration of 2,3-butanediol in the present invention can be carried out by gas-phase flow reaction. The gas-phase flow reaction is a reaction mode in which a solid catalyst is packed in a tubular reactor, and a vaporized raw material is allowed to flow through the catalyst layer to allow the reaction to proceed. Specific examples of the gas-phase flow reaction include the fixed-bed flow-type reaction in which the catalyst is left to stand, the moving-bed flow-type reaction in which the catalyst is moved, and the fluidized-bed flow-type reaction in which the catalyst is allowed to fluidize. To the gas-phase flow reaction in the present invention, any of these reaction modes may be applied.

In the gas-phase flow reaction, a vaporized raw material may be allowed to flow through the catalyst layer together with a carrier gas. The carrier gas is not limited, and preferred examples of the carrier gas include inert gases such as nitrogen, helium, and argon; hydrogen; and mixed gases of two or more of these. The carrier gas may contain water vapor, air, oxygen, and/or the like.

For example, as a fixed-bed flow-type reactor, the apparatus shown in FIG. 1 may be used. The apparatus in FIG. 1 is constituted by a reaction tube 1 having a raw material inlet 4 and a carrier-gas inlet 3; a reaction crude liquid collection container (condenser) 5; and a tubular furnace 2. A catalyst layer 6 can be fixed in the reaction tube 1. The reaction tube 1 can be heated to a desired temperature by the tubular furnace 2. The gas-phase flow reaction using the apparatus of FIG. 1 can be carried out by supplying the carrier gas and the raw material from the carrier-gas inlet 3 and the raw material inlet 4, respectively, to introduce them into the reaction tube 1. Condensable liquid compounds can be collected into the reaction crude liquid collection container 5, and uncondensable gas components can be recovered from a gas vent 7.

The reaction temperature during the step of dehydration of 2,3-butanediol is preferably not less than 380° C. and not more than 520° C. In cases where the reaction temperature is below the range described above, the conversion of 2,3-butanediol may be insufficient, while in cases where the reaction temperature exceeds the range described above, $C_1$-$C_4$ hydrocarbons may be generated as by-products, and the selectivity of butadiene, which is the product of interest, may be insufficient.

In the step of dehydration of 2,3-butanediol, the weight hourly space velocity (WHSV) of the raw material gas supplied into the reactor is not limited. The weight hourly space velocity is preferably not less than 0.1 $h^{-1}$ and not more than 10 $h^{-1}$, more preferably not less than 0.5 $h^{-1}$ and not more than 3 h$^{-1}$. The WHSV herein indicates the weight of 2,3-butanediol supplied per unit weight of the catalyst per unit time.

In the step of dehydration of 2,3-butanediol, the reaction pressure is not limited. The reaction pressure is preferably not less than 0.01 MPa and not more than 0.5 MPa. The reaction can be simply carried out under atmospheric pressure since, in such a case, the reaction does not require use of a device or operation for reducing or increasing the pressure.

As described above, a method for production of butadiene by dehydration reaction of 2,3-butanediol has also been disclosed in Patent Document 2. In this document, a cesium oxide-supporting silica catalyst is used at a reaction temperature of 400° C. In a reproducibility study by the present inventors, it was found that use of the catalyst in the above document leads to low selectivity of butadiene (see Comparative Example 7). On the other hand, in the method of the present invention using a catalyst containing an alkali metal salt of phosphoric acid and silica, butadiene can be produced with favorable selectivity.

The butadiene generated in the step of dehydration of 2,3-butadiene can be separated and purified by a known technique such as the method described in JP 45-17407 B, JP 60-126235 A, JP 3-48891 B, or WO 2012/157495.

EXAMPLES

The present invention is described below in more detail by way of Examples. However, the present invention is not limited to the Examples.

Catalyst Preparation

An example of the method for preparing silica on which an alkali metal dihydrogen phosphate is supported described below.

In an aqueous solution prepared by dissolving NaH$_2$PO$_4$ (0.55 g) in 50 g of water, 5 g of silica (Silica Gel 60 (Merck); 70-230 mesh; BET specific surface area, 500 m$^2$/g; hereinafter referred to as "SiO$_2$ (A)") was added, and the resulting mixture was stirred at room temperature for 1 hour. Using an evaporator, water was evaporated at 30 hPa at 40° C., and the resulting powder was dried at 80° C. for 5 hours. Thereafter, the powder was subjected to calcination under air flow at 450° C. for 6 hours. After kneading of 5 g of the powder with 1 g of Metrose SH65-3000 (Shin-Etsu Chemical Co., Ltd.), which is a cellulose-based binder, and 4 g of water, extrusion granulation was carried out using a 1-mm sieve, followed by performing calcination under air flow at 500° C. for 4 hours, thereby obtaining a catalyst. The resulting catalyst is hereinafter represented as "10% NaH$_2$PO$_4$/SiO$_2$ (A)". The ratio "10%" herein means that, before NaH$_2$PO$_4$ is supported on the silica (before the impregnation of the silica with NaH$_2$PO$_4$, and the drying and the calcination of the resultant), the ratio of NaH$_2$PO$_4$ to the total weight of NaH$_2$PO$_4$ and silica is 10 wt %.

In a similar manner, "10% KH$_2$PO$_4$/SiO$_2$ (A)", "10% RbH$_2$PO$_4$/SiO$_2$ (A)", "5% CsH$_2$PO$_4$/SiO$_2$ (A)", "10% CsH$_2$PO$_4$/SiO$_2$ (A)", "20% CsH$_2$PO$_4$/SiO$_2$ (A)", "30% CsH$_2$PO$_4$/SiO$_2$ (A)", and "40% CsH$_2$PO$_4$/SiO$_2$ (A)" were prepared as catalysts containing an alkali metal dihydrogen phosphate other than NaH$_2$PO$_4$ carried on silica.

SiO$_2$ (B) (CARiACT Q-6 (Fuji Silysia Chemical Ltd.); BET specific surface area, 536 m$^2$/g), SiO$_2$ (C) (CARPLEX BS303 (DSL Japan); BET specific surface area, 562 m$^2$/g), SiO$_2$ (D) (M. S. GEL D70 120A (AGC Si-Tech. Co., Ltd.); BET specific surface area, 450 m$^2$/g), SiO$_2$ (E) (Silica Gel 60 (Kanto Chemical Co., Inc.); BET specific surface area, 700 m$^2$/g), SiO$_2$ (F) (Aerolyst 3041 (Evonik Industries AG); BET specific surface area, 160 m$^2$/g), and SiO$_2$ (G) (Aerolyst 3045 (Evonik Industries AG); BET specific surface area, 160 m$^2$/g) were used as silica supports instead of SiO$_2$ (A), to prepare "10% CsH$_2$PO$_4$/SiO$_2$ (B)", "10% CsH$_2$PO$_4$/SiO$_2$ (C)", "10% CsH$_2$PO$_4$/SiO$_2$ (D)", "10% CsH$_2$PO$_4$/SiO$_2$ (E)", "10% CsH$_2$PO$_4$/SiO$_2$ (F)", and "10% CsH$_2$PO$_4$/SiO$_2$ (G)", respectively.

Magnesia (MgO, reference catalyst JRC-MGO3 of Catalysis Society of Japan), titania (TiO$_2$, Wako Pure Chemical Industries, Ltd.), alumina (Al$_2$O$_3$, reference catalyst JRC-ALO-6 of Catalysis Society of Japan), and zirconia (ZrO$_2$, reference catalyst JRC-ZRO-3 of Catalysis Society of Japan) were used instead of the silica described above (SiO$_2$ (A), Merck, Silica Gel 60, 70-230 mesh), to prepare "10% CsH$_2$PO$_4$/MgO", "10% CsH$_2$PO$_4$/TiO$_2$", "10% CsH$_2$PO$_4$/Al$_2$O$_3$", and "10% CsH$_2$PO$_4$/ZrO$_2$", respectively, as catalysts to be used in Comparative Examples.

Dehydration Reaction of 2,3-Butanediol

The dehydration reactions of 2,3-butanediol in the following Examples and Comparative Examples were carried out using the fixed-bed flow-type reactor shown in FIG. 1 composed of a Y-shaped quartz reaction tube 1 having an inner diameter of 15 mm and a total length of 350 mm, and a ceramic electric tubular furnace 2 (ARF-20KC, Asahi Rika Seisakusho Co., Ltd.). In an upper portion of the reaction tube, a carrier-gas inlet 3 and a raw material inlet 4 are provided, and a reaction crude liquid collection container 5 having a gas vent is connected to a lower portion of the reaction tube. The catalyst was packed into the central portion of the reaction tube, and fixed by sandwiching between silica wool (6). The crude liquid recovered in the collection container cooled in an ice bath was diluted with methanol to attain a final volume of 20 ml (in the cases of Examples 1 to 10 and Comparative Examples 1 to 7) or 10 ml (in the cases of Examples 11 to 17), and the resulting dilution was subjected to quantification by gas chromatography measurement. The gas product that had not undergone condensation in the collection container cooled in the ice bath was analyzed with a gas chromatography apparatus directly connected to the gas vent 7. Quantification of the raw material and the product was carried out based on an absolute calibration curve prepared using standard samples. The conversion (mol %) of 2,3-butanediol and the selectivity (mol %) of each product were calculated according to the following calculation equations (Equation 1) and (Equation 2), respectively.

Conversion (mol %)=(amount of raw material–remaining amount of raw material)/amount of raw material×100 (Equation 1)

Selectivity (mol %)=(yield of product)/(amount of raw material–remaining amount of raw material)×100 (Equation 2)

Analysis of Amount of Metal Impurities in Silica Support

In the presence of sulfuric acid, the silica support to be analyzed was dissolved by addition of hydrofluoric acid. The resultant was heated to remove the hydrofluoric acid and to allow vaporization of the silica, and dilute nitric acid was then added thereto. The resulting solution was subjected to quantification of the metal impurity concentration by atomic absorption spectrometry and ICP emission spectrometry. For these analyses, an atomic absorption spectrometer (AA-6200, Shimadzu Corporation) and an ICP emission analyzer (Optima 4300DV, Perkin Elmer) were used.

The metal content per unit surface area of the silica support (ng/m$^2$) was calculated by dividing the metal impurity concentration determined by the above measurement by the BET specific surface area of the silica. The calculated values are shown in Table 2.

Example 1

In the reaction tube, 10% $NaH_2PO_4/SiO_2$ (A) (1.0 g) was packed, and nitrogen was fed from the upper portion of the reaction tube at 30 ml/min. The tubular furnace was heated to 500° C., and left to stand at this temperature for 1 hour, followed by feeding 2,3-butanediol (Tokyo Chemical Industry Co., Ltd.; 63% meso-2,3-butanediol, 29% (2R,3R)-2,3-butanediol; 8% (2S,3S)-2,3-butanediol) to the catalyst layer from the upper portion of the reaction tube at 2 ml/h (WHSV: 1.97 $h^{-1}$) together with nitrogen gas flow. The reaction was allowed to proceed for 5 hours, and the conversion of 2,3-butanediol and the selectivity of each product were calculated. The results are shown in Table 1.

Example 2

The reaction was carried out in the same manner as in Example 1 except that 10% $KH_2PO_4/SiO_2$ (A) was used as the catalyst. The results are shown in Table 1.

Example 3

The reaction was carried out in the same manner as in Example 1 except that 10% $RbH_2PO_4/SiO_2$ (A) was used as the catalyst. The results are shown in Table 1.

Example 4

The reaction was carried out in the same manner as in Example 1 except that 10% $CsH_2PO_4/SiO_2$ (A) was used as the catalyst. The results are shown in Table 1.

Example 5

The reaction was carried out in the same manner as in Example 1 except that 5% $CsH_2PO_4/SiO_2$ (A) was used as the catalyst. The results are shown in Table 1.

Example 6

The reaction was carried out in the same manner as in Example 1 except that 20% $CsH_2PO_4/SiO_2$ (A) was used as the catalyst. The results are shown in Table 1.

Example 7

The reaction was carried out in the same manner as in Example 1 except that 30% $CsH_2PO_4/SiO_2$ (A) was used as the catalyst. The results are shown in Table 1.

Example 8

The reaction was carried out in the same manner as in Example 1 except that 40% $CsH_2PO_4/SiO_2$ (A) was used as the catalyst. The results are shown in Table 1.

Example 9

The reaction was carried out in the same manner as in Example 4 except that the reaction temperature was 400° C. The results are shown in Table 1.

Example 10

The reaction was carried out in the same manner as in Example 4 except that the reaction temperature was 450° C. The results are shown in Table 1.

Comparative Example 1

The reaction was carried out in the same manner as in Example 1 except that 10% $CsH_2PO_4/MgO$ was used as the catalyst. The results are shown in Table 1.

Comparative Example 2

The reaction was carried out in the same manner as in Example 1 except that 10% $CsH_2PO_4/TiO_2$ was used as the catalyst. The results are shown in Table 1.

Comparative Example 3

The reaction was carried out in the same manner as in Example 1 except that 10% $CsH_2PO_4/Al_2O_3$ was used as the catalyst. The results are shown in Table 1.

Comparative Example 4

The reaction was carried out in the same manner as in Example 1 except that 10% $CsH_2PO_4/ZrO_2$ was used as the catalyst. The results are shown in Table 1.

Comparative Example 5

By heating $CsH_2PO_4$ (6.9 g, Mitsuwa Chemicals Co., Ltd.) at 500° C. under air flow using an electric furnace (KDF-S70G, Denken), white crystals (6.4 g) were obtained. The crystals were then mildly crushed in a mortar to obtain a dehydrated condensate of $CsH_2PO_4$. The catalyst obtained is hereinafter represented as $CsH_2PO_4$-500 (the alkali metal salt of phosphoric acid used as the raw material—heating temperature (° C.)).

Dehydration reaction of 2,3-butanediol was carried out in the same manner as in Example 1 except that $CsH_2PO_4$-500 was used as the catalyst. The results are shown in Table 1.

Comparative Example 6

The reaction was carried out in the same manner as in Example 1 except that $SiO_2$ (A) calcined at 500° C. under air flow was used as the catalyst. The results are shown in Table 1.

Comparative Example 7

According to Patent Document 2, a cesium oxide-silica complex was prepared. $Cs_2CO_3$ (4.65 g, Wako Pure Chemical Industries, Ltd.) was dissolved in water (50 ml), and silica gel (Davisil (registered trademark), 35-60 mesh, Sigma-Aldrich, 10 g) was impregnated with the obtained aqueous solution. The resulting solution was heated with stirring at 80° C. for 24 hours for evaporation of water and drying. The resulting powder was calcined at 600° C. under air flow to obtain the cesium oxide-silica complex (13.1 g). The reaction was carried out in the same manner as in Example 1 except that the cesium oxide-silica complex (5.0 g) was used as the catalyst, and that the reaction temperature was 400° C. The results are shown in Table 1.

TABLE 1

| | Catalyst | Reaction temperature (° C.) | Conversion (mol %) | Selectivity (mol %) | | | | | |
|---|---|---|---|---|---|---|---|---|---|
| | | | | Methyl ethyl ketone | Butadiene | 3-Buten-2-ol | Isobutyl aldehyde | Butene | Others |
| Example 1 | 10%NaH$_2$PO$_4$/SiO$_2$(A) | 500 | >99.9 | 27.5 | 64.6 | N.D. | 3.9 | 2.6 | 1.5 |
| Example 2 | 10%KH$_2$PO$_4$/SiO$_2$(A) | 500 | >99.9 | 19.0 | 74.1 | 0.1 | 2.2 | 4.4 | 0.3 |
| Example 3 | 10%RbH$_2$PO$_4$/SiO$_2$(A) | 500 | 98.0 | 14.8 | 77.8 | 1.5 | 1.6 | 4.2 | 0.1 |
| Example 4 | 10%CsH$_2$PO$_4$/SiO$_2$(A) | 500 | 99.9 | 11.9 | 74.9 | 0.7 | 0.9 | 11.4 | 0.2 |
| Example 5 | 5%CsH$_2$PO$_4$/SiO$_2$(A) | 500 | >99.9 | 16.6 | 66.9 | 0.8 | 1.1 | 10.9 | 3.7 |
| Example 6 | 20%CsH$_2$PO$_4$/SiO$_2$(A) | 500 | 94.8 | 10.7 | 71.8 | 4.4 | 2.0 | 8.0 | 3.2 |
| Example 7 | 30%CsH$_2$PO$_4$/SiO$_2$(A) | 500 | 98.4 | 10.5 | 73.7 | 7.2 | 1.6 | 5.2 | 1.8 |
| Example 8 | 40%CsH$_2$PO$_4$/SiO$_2$(A) | 500 | 99.3 | 10.6 | 71.9 | 10.3 | 1.8 | 2.7 | 2.8 |
| Example 9 | 10%CsH$_2$PO$_4$/SiO$_2$(A) | 400 | 94.8 | 20.5 | 70.0 | 6.6 | 1.3 | 0.5 | 1.2 |
| Example 10 | 10%CsH$_2$PO$_4$/SiO$_2$(A) | 450 | 99.2 | 14.7 | 73.8 | 5.5 | 1.2 | 4.6 | 0.3 |
| Comparative Example 1 | 10%CsH$_2$PO$_4$/MgO | 500 | 99.9 | 47.4 | 18.5 | 8.2 | 5.9 | 9.7 | 10.2 |
| Comparative Example 2 | 10%CsH$_2$PO$_4$/TiO$_2$ | 500 | 57.6 | 17.2 | 6.1 | 19.2 | 5.6 | 50.3 | 1.6 |
| Comparative Example 3 | 10%CsH$_2$PO$_4$/Al$_2$O$_3$ | 500 | >99.9 | 36.3 | 25.1 | N.D. | 3.3 | 17.8 | 17.4 |
| Comparative Example 4 | 10%CsH$_2$PO$_4$/ZrO$_2$ | 500 | >99.9 | 36.9 | 38.1 | 0.5 | 4.0 | 11.9 | 8.7 |
| Comparative Example 5 | CsH$_2$PO$_4$-500 | 500 | 73.4 | 9.9 | 42.7 | 31.7 | 2.9 | 10.9 | 2.0 |
| Comparative Example 6 | SiO$_2$(A) | 500 | >99.9 | 34.6 | 47.5 | N.D. | 7.3 | 6.2 | 4.5 |
| Comparative Example 7 | Cesium oxide-silica complex | 400 | 86.4 | 7.6 | 18.4 | 23.9 | 9.1 | 10.0 | 22.6 |

Example 11

In the reaction tube, 10% CsH$_2$PO$_4$/SiO$_2$ (A) (1.0 g) was packed, and nitrogen was fed from the upper portion of the reaction tube at 30 ml/min. The tubular furnace was heated to 405° C., and left to stand at this temperature for 1 hour, followed by feeding 2,3-butanediol (Tokyo Chemical Industry Co., Ltd.; 63% meso-2,3-butanediol; 29% (2R,3R)-2,3-butanediol; 8% (2S,3S)-2,3-butanediol) to the catalyst layer from the upper portion of the reaction tube at 1 ml/h (WHSV: 0.98 h$^{-1}$) together with nitrogen gas flow. One hour after the feed of 2,3-butanediol was defined as the start time of the reaction (Hour 0). The reaction was allowed to proceed for 8 hours, and the butadiene selectivities between Hours 0 and 1 and between Hours 7 and 8 were calculated. In addition, as an index of a decrease in the selectivity, the change in the butadiene selectivity was calculated according to Equation 3. The results are shown in Table 2.

Change in butadiene selectivity=(butadiene selectivity between Hours 7 and 8)−(butadiene selectivity between Hours 0 and 1)  (Equation 3)

Example 12

The reaction was carried out in the same manner as in Example 11 except that 10% CsH$_2$PO$_4$/SiO$_2$ (B) was used as the catalyst. The results are shown in Table 2.

Example 13

The reaction was carried out in the same manner as in Example 11 except that 10% CsH$_2$PO$_4$/SiO$_2$ (C) was used as the catalyst. The results are shown in Table 2.

Example 14

The reaction was carried out in the same manner as in Example 11 except that 10% CsH$_2$PO$_4$/SiO$_2$ (D) was used as the catalyst. The results are shown in Table 2.

Example 15

The reaction was carried out in the same manner as in Example 11 except that 10% CsH$_2$PO$_4$/SiO$_2$ (E) was used as the catalyst. The results are shown in Table 2.

Example 16

The reaction was carried out in the same manner as in Example 11 except that 10% CsH$_2$PO$_4$/SiO$_2$ (F) was used as the catalyst. The results are shown in Table 2.

Example 17

The reaction was carried out in the same manner as in Example 11 except that 10% CsH$_2$PO$_4$/SiO$_2$ (G) was used as the catalyst. The results are shown in Table 2.

TABLE 2

| | | Butadiene selectivity (mol %) | | | Metal content per unit surface area of the silica support (ng/m$^2$) | | |
|---|---|---|---|---|---|---|---|
| | Catalyst | Hour 0-Hour 1 | Hour 7-Hour 8 | Change in the butadiene selectivity (mol %) | Aluminum | Titanium | Total content of titanium and aluminum |
| Example 11 | 10%CsH$_2$PO$_4$/SiO$_2$(A) | 89.3 | 84.5 | −4.8 | 800 | 240 | 1040 |
| Example 12 | 10%CsH$_2$PO$_4$/SiO$_2$(B) | 91.8 | 89.4 | −2.4 | 131 | 174 | 305 |
| Example 13 | 10%CsH$_2$PO$_4$/SiO$_2$(C) | 90.9 | 84.7 | −6.2 | 694 | 164 | 858 |
| Example 14 | 10%CsH$_2$PO$_4$/SiO$_2$(D) | 88.5 | 89.7 | +1.1 | 200 | 222 | 422 |

TABLE 2-continued

| | | Butadiene selectivity (mol %) | | | Metal content per unit surface area of the silica support (ng/m$^2$) | | |
|---|---|---|---|---|---|---|---|
| | Catalyst | Hour 0-Hour 1 | Hour 7-Hour 8 | Change in the butadiene selectivity (mol %) | Aluminum | Titanium | Total content of titanium and alumimim |
| Example 15 | 10%CsH$_2$PO$_4$/SiO$_2$(E) | 82.6 | 79.6 | −3.0 | 61 | 104 | 165 |
| Example 16 | 10%CsH$_2$PO$_4$/SiO$_2$(F) | 86.4 | 85.4 | −1.0 | 21 | 16 | 37 |
| Example 17 | 10%CsH$_2$PO$_4$/SiO$_2$(G) | 83.5 | 76.0 | −7.5 | 24 | 750 | 774 |

Examples 1 to 10 showed that, in cases where 2,3-butanediol is dehydrated in the presence of a catalyst containing an alkali metal salt of phosphoric acid supported on silica, by-production of methyl ethyl ketone is suppressed, and the selectivity of butadiene increases. In particular, it was shown that use of a catalyst in which the alkali metal is K, Rb, or Cs leads to an even higher butadiene selectivity. It was also shown, according to Comparative Example 7, that the butadiene selectivities obtained in the present invention are much higher than those in known technologies.

Example 4 and Comparative Examples 1 to 4, showed that, in cases where a catalyst containing an alkali metal dihydrogen phosphate supported on silica is used, the selectivity of butadiene is high. Further, from Comparative Examples 5 and 6, it was shown that the alkali metal dihydrogen phosphate needs to be carried on the silica in order to achieve the high butadiene selectivity.

Examples 4 to 8 showed that high butadiene selectivity can be achieved by using a catalyst in which, during the preparation of the catalyst, the ratio of the alkali metal dihydrogen phosphate to the total weight of the silica and the alkali metal dihydrogen phosphate is not less than 5 wt % and not more than 40 wt %.

Examples 4, 9, and 10 showed that butadiene can be produced with high selectivity at a reaction temperature of 400° C. to 500° C.

Examples 11 to 17 showed that butadiene can be produced with high selectivity by using a catalyst containing a silica support having a total content of titanium and aluminum per unit surface area of not more than 1100 ng/m$^2$.

Since the changes in the butadiene selectivity in Examples 12, 14, 15, and 16 were smaller than the changes in the butadiene selectivity in Examples 11, 13, and 17 in terms of the degree of reduction of the butadiene selectivity, it was shown that high butadiene selectivity can be maintained for a long time by using a catalyst containing a silica support having a total content of titanium and aluminum per unit surface area of not more than 750 ng/m$^2$.

INDUSTRIAL APPLICABILITY

By the present invention, butadiene can be produced with high selectivity from 2,3-butanediol, which is derivable from biomass resources, without using a radioactive substance. The present invention enables replacement of the raw material of butadiene from fossil resources to biomass resources. The present invention is industrially extremely useful since butadiene is a raw material for industrial chemicals such as synthetic rubbers and plastics.

DESCRIPTION OF SYMBOLS

1 Reaction tube
2 Electric tubular furnace
3 Carrier-gas inlet
4 Raw material inlet
5 Reaction crude liquid collection container (condenser)
6 Catalyst layer
7 Gas vent

The invention claimed is:
1. A method for producing butadiene, said method comprising dehydrating 2,3-butanediol in the presence of a catalyst containing an alkali metal dihydrogen phosphate supported on silica to produce a product stream containing butadiene.
2. The method according to claim 1, wherein a weight ratio of said alkali metal dihydrogen phosphate to the total weight of said silica and said alkali metal dihydrogen phosphate in said catalyst is not less than 5 wt % and not more than 40 wt % before supporting said alkali metal dihydrogen phosphate on said silica.
3. The method according to claim 1, wherein the alkali metal in said alkali metal dihydrogen phosphate is one or more selected from the group consisting of K, Rb, and Cs.
4. The method according to claim 1, wherein said alkali metal dihydrogen phosphate is supported on said silica by calcination of silica to which alkali metal dihydrogen phosphate was attached.
5. The method according to claim 1, wherein a reaction temperature of the dehydrating 2,3-butanediol is not less than 380° C. and not more than 520° C.

* * * * *